US00PP15757P3

(12) United States Plant Patent
Hofmann et al.

(10) Patent No.: US PP15,757 P3
(45) Date of Patent: May 10, 2005

(54) *NEMESIA* PLANT NAMED 'INNKABLUE'

(50) Latin Name: *Nemesia hybrida*
Varietal Denomination: Innkablue

(76) Inventors: Silvia Hofmann, Engel Strasse 72, 55124 Mainz (DE); Susanne Herdegen, Am Dreschacker 41, D-55278 Dexheim (DE); Hendrik Theobald, Bahnhofstrasse 36, 55262 Heidesheim (DE)

( * ) Notice: Subject to any disclaimer, the term of this patent is extended or adjusted under 35 U.S.C. 154(b) by 2 days.

(21) Appl. No.: 10/839,209

(22) Filed: May 5, 2004

(65) Prior Publication Data

US 2004/0205871 P1 Oct. 14, 2004

(51) Int. Cl.[7] ..... A01H 5/00

(52) U.S. Cl. ..... Plt./263

(58) Field of Search ..... Plt./263

(56) References Cited

PUBLICATIONS

UPOV–Rom, Plant Variety Database, hits on 'Innkablue', GTI Jouve, 2004/02.*

* cited by examiner

*Primary Examiner*—Anne Marie Grunberg
(74) *Attorney, Agent, or Firm*—C. A. Whealy

(57) ABSTRACT

A new and distinct cultivar of *Nemesia* plant named 'Innkablue', characterized by its upright, outwardly spreading to trailing plant habit; vigorous growth habit; freely branching habit; and numerous dark violet-colored flowers.

1 Drawing Sheet

Botanical classification/cultivar designation: *Nemesia hybrida* cultivar Innkablue.

BACKGROUND OF THE INVENTION

The present invention relates to a new and distinct cultivar of *Nemesia* plant, botanically known as *Nemesia hybrida* and referred to by the name 'Innkablue'.

The new *Nemesia* is a product of a planned breeding program conducted by the Inventors in Gensingen, Germany. The objective of the program is to create new compact *Nemesia* cultivars with numerous flowers, unique flower colors and fragrance.

The new *Nemesia* originated from a cross by the Inventors of a proprietary *Nemesia* hybrid selection identified as code N98Sä3tetra2, not patented, as the female, or seed, parent with the *Nemesia* hybrid cultivar Hubbird, disclosed in U.S. Plant Pat. No. 12,014, as the male, or pollen, parent during the summer of 1999. The cultivar Innkablue was discovered and selected by the Inventors as a flowering plant within the progeny of the stated cross in a controlled environment in Gensingen, Germany during the summer of 1999.

Asexual reproduction of the new *Nemesia* by terminal cuttings taken in a controlled environment in Gensingen, Germany since 1999, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Innkablue' and distinguish 'Innkablue' as a new and distinct cultivar:

1. Upright, outwardly spreading to trailing plant habit.
2. Vigorous growth habit.
3. Freely branching habit.
4. Numerous dark violet-colored flowers.

Plants of the new *Nemesia* differ primarily from plants of the female parent selection in the following characteristics:

1. Plants of the new *Nemesia* flower earlier than plants of the female parent selection.
2. Plants of the new *Nemesia* have larger flowers than plants of the female parent selection.
3. Plants of the new *Nemesia* are more freely flowering than plants of the female parent selection.

Plants of the new *Nemesia* are most similar to plants of the male parent, the cultivar Hubbird. Plants of the new *Nemesia* differ from plants of the cultivar Hubbird in the following characteristics:

1. Plants of the new *Nemesia* are more vigorous than plants of the cultivar Hubbird.
2. Plants of the new *Nemesia* have larger flowers than plants of the cultivar Hubbird.
3. Flowers of plants of the new *Nemesia* are more fragrant than flowers of plants of the cultivar Hubbird.
4. Flowers of plants of the new *Nemesia* are more intense dark violet in color than flowers of plants of the cultivar Hubbird.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia*.

The photograph at the bottom of the sheet comprises a side perspective view of a typical potted plant of 'Innkablue' that was about ten weeks old.

The photograph at the top of the sheet comprises a close-up view of typical flowers of 'Innkablue'.

DETAILED BOTANICAL DESCRIPTION

The aforementioned photographs and following observations and averaged measurements describe plants grown in Bonsall, Calif., in an outdoor nursery during the spring with day temperatures ranging from 18 to 35° C. and night temperatures ranging from 7 to 18° C. After rooting, plants were grown for about ten weeks in 15-cm containers with one plant per container. Color references are made to The Royal Horticultural Society Colour Chart, 1995 Edition, except where general terms of ordinary dictionary significance are used.

Botanical classification: *Nemesia hybrida* cultivar Innkablue.

Parentage:

*Female parent.*—Proprietary *Nemesia* hybrid selection identified as code N98Sä3tetra2, not patented.

*Male parent.*—*Nemesia* hybrid cultivar Hubbird, disclosed in U.S. Plant Pat. No. 12,014.

Propagation:

*Type.*—By vegetative cuttings.

*Time to initiate roots.*—About 10 to 14 days at 20° C.

*Time to develop roots.*—About two to three weeks at 20° C.

*Root description.*—Fibrous, fine; white in color.

Plant description:

*General appearance.*—Upright, outwardly spreading to trailing plant habit; broad inverted triangle. Freely branching, typically about 14 primary lateral branches and about three or four secondary lateral branches per primary lateral branch. Numerous dark violet-colored zygomorphic flowers. Vigorous growth habit.

*Plant height.*—About 23 cm.

*Plant diameter or spread.*—About 39 cm.

*Lateral branches.*—Appearance: Square in cross-section with longitudinal ridges. Length: About 22 cm. Diameter: About 4 mm. Internode length: About 3 to 3.5 cm. Strength: Strong. Texture: Smooth, glabrous. Color: 146A.

*Foliage description.*—Arrangement: Opposite, simple. Shape: Elliptic. Apex: Broadly acute. Base: Attenuate. Length: About 5.5 cm. Width: About 3.5 cm. Margin: Broadly serrate. Texture, upper and lower surfaces: Smooth, glabrous. Venation pattern: Pinnate, arcuate. Petiole length: About 4 mm. Petiole diameter: About 5 mm. Color: Developing and fully expanded leaves, upper surface: 147A. Developing and fully expanded leaves, lower surface: 147B. Venation, upper and lower surfaces: 147B. Petiole: 146A.

Flowering description:

*Arrangement/appearance.*—Zygomorphic bilabiate solitary flowers arranged on terminal racemes; flowering acropetally towards apex. Flowers face mostly outward. Flowers last about five days on the plant. Flowers not persistent.

*Natural flowering season.*—Natural flowering season is spring to fall; flowering continuous during this period.

*Quantity of flowers.*—Freely flowering with about 20 to 26 open flowers and flower buds per raceme at one time.

*Fragrance.*—None detected.

*Inflorescence length.*—About 15 cm.

*Inflorescence diameter.*—About 5.5 cm.

*Flower diameter.*—About 2 cm.

*Flower depth, including nectar spur.*—About 1.5 cm.

*Flower buds.*—Shape: Ovoid with spur. Length including spur: About 7 mm. Diameter: About 6 mm. Color: More gray than 186C.

*Petals.*—Arrangement/shape: Five petals total. Four upper petals are fused at base to form an upright lobed and arched banner lip; lower petal modified into a larger lip with nectar spur and convex oval protuberance which serves as pollinator nectar guide and landing platform. Shape: Oval to oblong. Apex: Rounded. Margin: Entire. Length: Upper petal: About 1 cm. Lateral petals: About 9 mm. Lower petal: About 1 cm. Width: Upper petal: About 6 mm. Lateral petals: About 8 mm. Lower petal: About 1.4 cm. Texture, upper and lower surfaces: Smooth, velvety. Color: When opening, upper surface: 83B. When opening, lower surface: More gray than 86D. Fully opened, upper surface: 83C; towards base narrow central ring, 155D. Fully opened, lower surface: More gray than 86D. Nectar guide: 3A. Nectar spur: 157A.

*Sepals.*—Quantity: Five-parted, star-shaped calyx. Shape: Elliptic. Apex: Acute. Base: Fused. Margin: Entire. Length: About 4 mm. Diameter: About 2 mm. Texture, upper and lower surfaces: Pubescent. Color, upper and lower surfaces: 146A.

*Peduncle.*—Length: About 4 cm. Diameter: About 2 mm. Strength: Strong. Angle: Upright to 45° from the stem. Color: 146A.

*Pedicel.*—Length: About 1 cm. Diameter: Less than 1 mm. Strength: Strong. Angle: About 45° from the stem. Color: 146A.

*Androecium.*—Stamen number: Four per flower. Anther shape: Oval. Anther size: Less than 1 mm. Anther color: 24A. Amount of pollen: Scarce. Pollen color: 24A.

*Gynoecium.*—Pistil number: One per flower. Pistil length: About 3 mm. Style length: About 1 mm. Style color: 145D. Stigma shape: Rounded. Stigma color: 145D. Ovary color: 145C.

*Seed/fruit.*—Seed and fruit production has not been observed on plants of the new *Nemesia*.

Disease/pest resistance: Plants of the new *Nemesia* have not been observed to be resistant to pathogens or pests common to *Nemesias*.

Temperature tolerance: Plants of the new *Nemesia* have been observed to be tolerant to temperatures ranging from 2° to 35° C.

It is claimed:

1. A new and distinct cultivar of *Nemesia* plant named 'Innkablue', as illustrated and described.

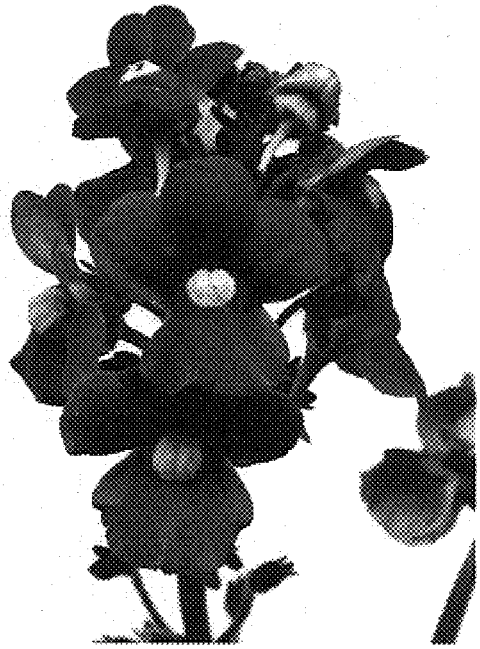
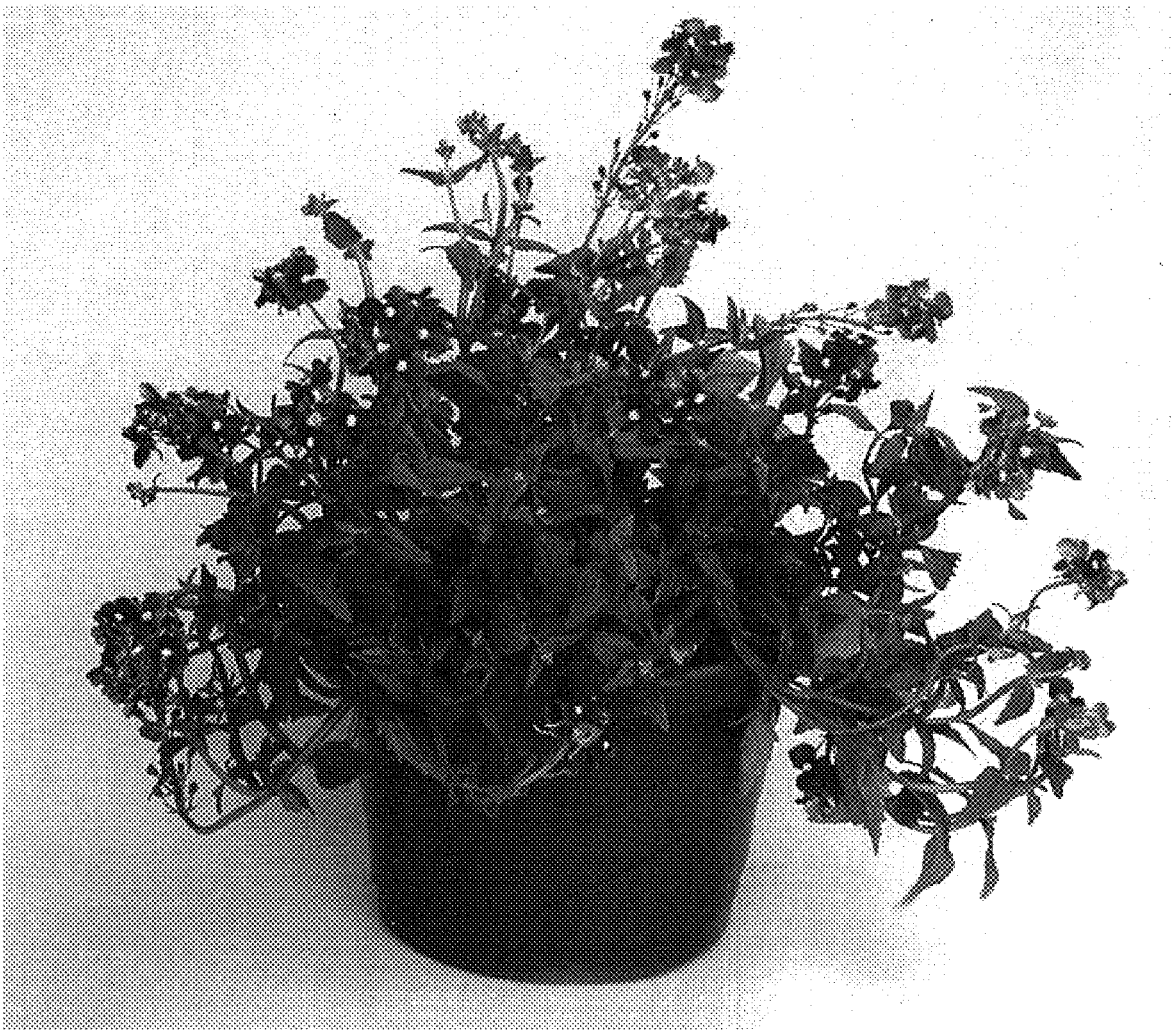

* * * * *